(12) United States Patent
Winter

(10) Patent No.: US 6,400,973 B1
(45) Date of Patent: Jun. 4, 2002

(54) ARTERIAL BLOOD FLOW SIMULATOR

(75) Inventor: Robert A. Winter, Sioux Falls, SD (US)

(73) Assignee: Bowden's Automated Products, Inc., SD (US)

(*) Notice: Subject to any disclaimer, the term of this patent is extended or adjusted under 35 U.S.C. 154(b) by 0 days.

(21) Appl. No.: 09/474,315

(22) Filed: Dec. 29, 1999

Related U.S. Application Data

(63) Continuation of application No. 09/009,086, filed on Jan. 20, 1998, now abandoned.

(51) Int. Cl.[7] .................................................. A61B 5/00
(52) U.S. Cl. ........................ 600/323; 600/324; 600/331
(58) Field of Search ................................. 600/309–310, 600/316, 322–324, 331, 336; 356/39–42; 434/268, 272

(56) References Cited

U.S. PATENT DOCUMENTS

| | | | |
|---|---|---|---|
| 4,869,254 A | | 9/1989 | Stone et al. |
| 4,968,137 A | * | 11/1990 | Yount ........................... 356/41 |
| 5,278,627 A | * | 1/1994 | Aoyagi et al. ................. 356/41 |
| 5,300,779 A | * | 4/1994 | Hillman et al. ............... 250/341 |
| 5,348,005 A | * | 9/1994 | Merrick et al. ............... 600/330 |
| 5,416,575 A | * | 5/1995 | Schwartz ..................... 356/243 |
| 5,784,151 A | * | 7/1998 | Miller et al. .................. 356/41 |
| 5,991,028 A | * | 11/1999 | Cabib et al. .................. 356/346 |

* cited by examiner

*Primary Examiner*—Eric F. Winakur
*Assistant Examiner*—Matthew Kremer
(74) *Attorney, Agent, or Firm*—Patnaude & Videbeck

(57) ABSTRACT

An artificial blood flow simulator to be used to test or calibrate a pulse oximeter has a body which is at least partially transparent to red and infrared light waves. Within the body is a light valve which is responsive to an electronic signal for varying the amount of light passing through the body. Connected to the light valve is a signal generator for generating a pulsating electronic signal which corresponds to a given blood flow. The device has the permeability of a human appendage between pulses of blood in the arterial system when the signal generator is generating an electronic pulse and has the permeability of an appendage having arterial blood flowing therethrough when the signal generator is not generating an electronic pulse.

7 Claims, 3 Drawing Sheets

ARTERIAL BLOOD FLOW SIMULATOR

This application is a continuation application Ser. No. 09/009,086 filed on Jan. 20, 1998 now abandoned.

The present invention relates to devices for testing the accuracy of a pulse oximeter, and in particular to a device for simulating a given percentage of oxygen saturation of blood flow and heart rate which can be measured by a pulse oximeter.

BACKGROUND OF THE INVENTION

In recent years, the pulse oximeter has become a useful diagnostic medical instrument for patient care which calculates the oxygen saturation of arterial blood to thereby monitor the patient's pulmonary system. The pulse oximeter measures the amount of light absorbed by arterial hemoglobin at red and infrared waveforms and establishes a ratio between the absorption rates of the two waveforms.

The pulse oximeter is described in many documents, including U.S. Pat. No. 4,869,254 and other references. Although there are several variations in the technology for the pulse oximeters, the current technology includes a light source for generating two given wavelengths of light, typically red and infrared, which is projected through a relatively thin appendage or body portion, such as a finger or earlobe. A light detector is positioned on the opposite side of the body portion, and the intensity of the light passing through the body portion for both wavelengths are measured. The absorption of light through a given medium, such as a portion of the human body, is an exponential factor of the distance traveled and, therefore, the theory of the pulse oximeter is based upon the mathematical relationship of the Beer-Lambert law.

The pulse oximeter typically produces two wavelengths of light which are capable of penetrating the thickness of the appendage around which the light source and detector have been positioned and which have a given absorption characteristic for oxygenated and de-oxygenated hemoglobin. One typical pulse oximeter employs wavelengths of light of 660 nanometers (red) and 880 nanometers (infrared) as wavelengths which are produceable from economically available sources and which have suitable absorption characteristics of oxygenated and de-oxygenated hemoglobin. The device then calculates an oxygen saturated ratio (ROS) which fluctuates in response to changes in the permeability of the media through which the light is directed. The changes in the permeability are caused by the changes in the oxygenation of the hemoglobin. When a patient's heart drives a pulse of oxygenated hemoglobin into the arterial structure of the appendage, the ROS for the appendage is different than when oxygenated blood is not being driven through the arterial system, and the differences of the ROS of the medium is caused solely by the presence of the oxygenated hemoglobin in the arterial system. An equation built into the device is used to calculate a measure of the oxygenation of the hemoglobin.

Since the pulse oximeter measures the light absorption for both oxygenated and unoxygenated blood, the device also calculates the patient's pulse rate and the pulse rate is displayed as an output of the device.

The usefulness of a diagnostic instrument such as a pulse oximeter lies only in its accuracy, and if a pulse oximeter is not properly calibrated it will not provide accurate readings, and the readings will mislead medical personnel who rely on the instrument and the benefit which would otherwise be achieved by the use of the instrument will, therefore, be lost. It is necessary, therefore, to test or calibrate a pulse oximeter.

An obvious method of testing or calibrating a pulse oximeter would be to provide a simulated human appendage having characteristics which duplicate the light absorptive qualities of a living appendage through which flow pulses of the arterial blood having a given percentage of oxygenation. Such a simulator must duplicate the light absorptive qualities of an appendage of the human body between pulses of blood through the arterial system and during pulses of blood through the arterial system such that the device can thereby measure the differences of light passing through the simulated appendage and calculate the simulated oxygenation of the hemoglobin.

Prior efforts to simulate a human appendage have resulted in a mechanically operated device such as manufactured by Nonin Medical Incorporated of Plymouth, Minn. which includes an elongate member simulating the finger of a patient to which is attached a compressible bulb which can be squeezed by the operator of the test equipment. When the bulb is not being compressed, the simulated finger has the light absorptive qualities of a human finger during intervals of time between pulses of oxygenated blood in the arterial system. When the bulb is compressed, a liquid is forced within the simulated finger which alters the light absorptive qualities of the simulated finger to that of a human finger which is receiving a pulse of blood through its arterial system. Such existing devices, however, cannot test the accuracy of the pulse rate measuring capabilities of the pulse oximeter being tested. It would be desirable, therefore, to provide an arterial blood flow simulator which can accurately simulate the pulsating changes in the absorptive qualities of a human appendage in response to given pulses rates of hemoglobin having a given oxygen saturation rate passing through the appendage.

BRIEF DESCRIPTION OF THE INVENTION

Briefly, the present invention is embodied in an artificial blood flow simulator to be used to test or calibrate a pulse oximeter. Briefly, the arterial blood flow simulator has a body comprising material which is at least partially transparent to red and infrared light waves. The body is shaped and sized like that of a human appendage which can be received between the light sources and the light sensors of a pulse oximeter. Within the body is a light valve which is responsive to an electronic signal for varying the amount of light passing through the body. Connected to the light valve is a signal generator for generating a pulsating electronic signal which corresponds to a given blood flow amplitude, that is, corresponds to blood flow having a given pulse rate and a given oxygenation of the hemoglobin in the arterial blood flow.

The device will have the permeability of a human appendage between pulses of blood in the arterial system when the signal generator is generating an electronic pulse and will have the permeability of an appendage having arterial blood flowing therethrough when the signal generator is not generating an electronic pulse.

BRIEF DESCRIPTION OF THE DRAWINGS

A better understanding of the present invention will be had after a reading of the following detailed description taken in conjunction with the following drawings wherein.

Detailed Description of the Preferred Embodiment

Figure 1:
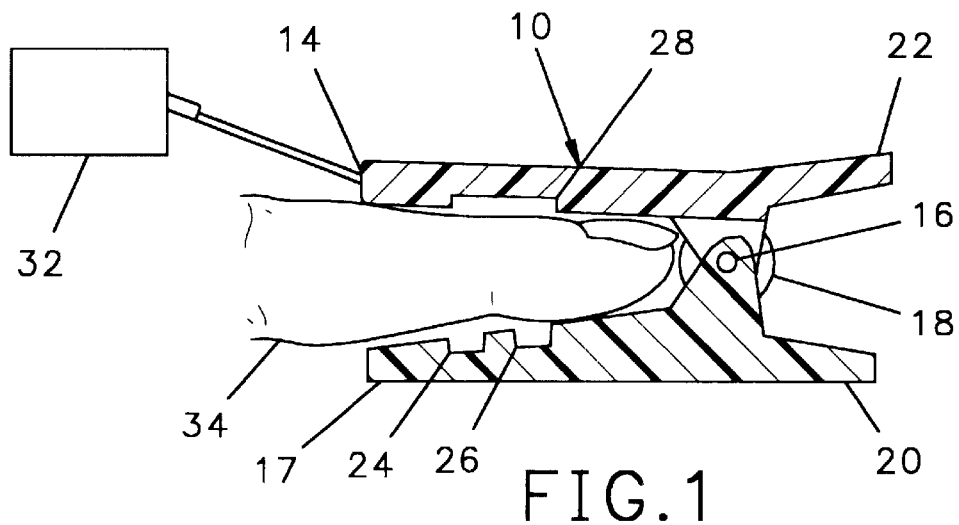
FIG. 1 is a cross-sectional view of the jaws of a pulse oximeter with the finger of a patient within its jaws.

Referring to FIG. 1, a pulse oximeter 10 has a pair of opposing jaws 12, 14 which are movable about a pin 16. A spring 18 urges the jaws 12, 14 towards each other such that the distal ends of the jaws will contact each other unless a force is applied to open the jaws 12, 14 or an obstruction is positioned between the jaws. Extending from the rearward end of the jaws 12, 14 are elongated projections 20, 22, respectively, which can be grasped by the fingers of an operator and squeezed to thereby open the jaws 12, 14. On one jaw 12 is a first LED 24 which generates light at a first given light wave, such as red light having a wave length of 660 nanometers, and a second LED 26 which generates light at a second given wavelength, such as infrared light having a wavelength of 880 nanometers. Positioned on the second jaw 14 is a sensor 28 for detecting the intensity of the light received from either the first LED 24 or the second LED 26. The sensor 28 is electrically connected into the circuit 32 which includes a microcomputer and a clock as described below. The circuit alternately illuminates the first LED 24 and second LED 26 such that the intensity of both light frequencies passing through an appendage 34 can be measured by the single sensor 28. The circuit 32 also measures the rate of the changes in the intensity of light passing through the appendage 34 to thereby determine a pulse rate. The changes in intensity of the lights received by the sensor 28 as a result of a pulse of oxygenated blood passing through the appendage 34 are compared in a formula within the device 10 to calculate the oxygen saturation rate.

Figure 2:
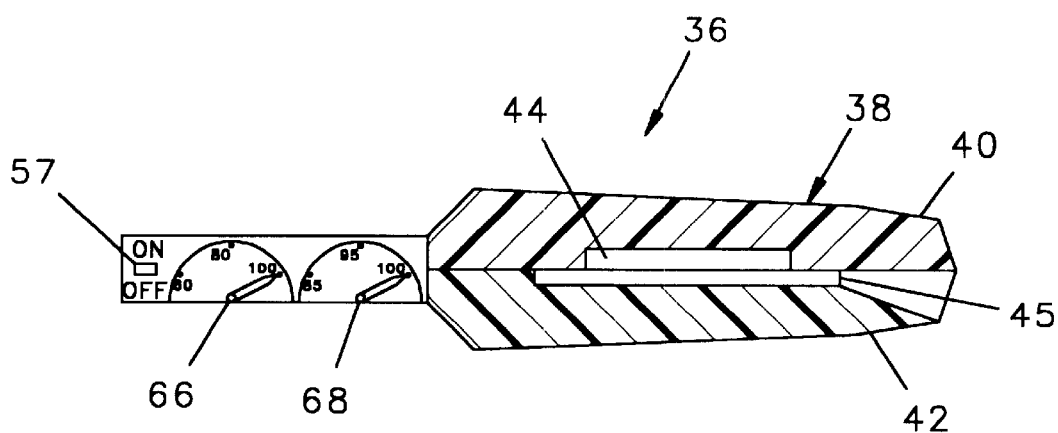
FIG. 2 is a cross-sectional view of an artificial finger for use with an arterial blood flow simulator in accordance with the present invention.

Referring to FIG. 2, to test the accuracy of the pulse oximeter 10, an artificial blood flow simulator 36 is provided having an artificial appendage 38 which may be inserted between the jaws 12, 14 of the pulse oximeter in place of the finger 34 of a patient. In accordance with the present invention, the body of the artificial appendage 38 is made of a suitable material such as a plastic. The body has an upper body portion 40 and a lower body portion 42 and sandwiched between the two portions is a light valve 44 and adjacent the light valve 44 is a red filter 45, as further described below.

The light valve 44 is a polymer dispersed liquid crystal, as further described below, which has a first, de-energized, state, or inactive state, in which the valve has a given light conductivity, and a second, energized, state, or active state, in which the valve has a second given light conductivity. When the light valve 44 is sandwiched between the upper body portion 40 and lower body portion 42, and the valve 44 is in the de-energized or inactive state, the artificial appendage 38 has a combined light conductivity of the portions 40, 42, 44 which is comparable to the light conductivity of the simulated human appendage which is receiving a pulse of oxygenated blood. When the light valve 44 is in the energized, or active state, the portions 40, 42, 44 of the simulated appendage 38 have a combined light conductivity comparable to the simulated human appendage is not receiving a pulse of oxygenated blood.

Polymer dispersion liquid crystals (PDLCS) consist of liquid crystal droplets dispersed in a polymer material. The molecules in the droplets of liquid crystal are responsive to an electric field. When the PDLC is not being subjected to an electric field, the liquid crystal droplets have a first conductivity to light, and when the PDLC is being subjected to an electric field, liquid crystal droplets have a second conductivity to light. Potentially, there are many configurations in which a PDLC can be employed to provide a light valve as disclosed in numerous references such as Drzaic, Polymer Dispersed Liquid Crystal for Large Area Displays and Light Values, J. Appl. Phys., vol. 60, pp. 2142–2148, 1986.

Figure 3:
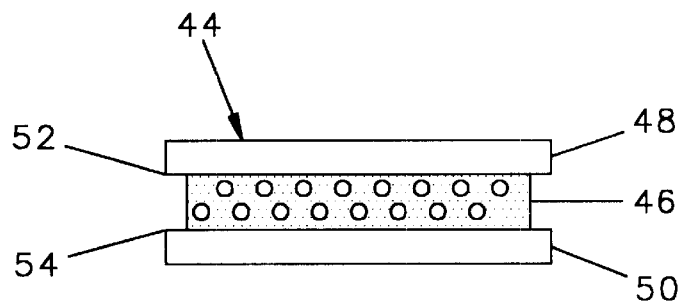
FIG. 3 is an enlarged cross sectional view of the light valve for use in an arterial blood flow simulator.

One embodiment of a light valve 44 is shown in FIG. 3 in which a PDLC film 46 is sandwiched between two plastic planar outer members 48, 50, respectively. The surfaces of the plastic members 48, 50, which abut against the PDLC film 46 are coated with thin layers 52, 54, respectively, of conductive material such as indium tin oxide. When a voltage is applied across the conductive layers 52, 54, an electric field will extend through the PDLC film and the liquid crystal molecules inside the droplets will align with the field. In this configuration when a voltage is applied to the layers 52, 54, the index of refraction of the PDLC layer is substantially equal to that of the polymer matrix and light passing through the PDLC 46 is not scattered causing the valve 44 to be substantially transparent to light. When the voltage is removed from the conductive films 52, 54, the orientation of the nematic liquid crystal molecules within the droplets of the PDLC becomes random and light directed toward the valve 44 will be backscattered and the valve will no longer be as transparent to light. In the preferred embodiment, the light valve 44 can reduce the transparency of the artificial appendage 38 to red light by approximately 15 percent.

Figure 4:
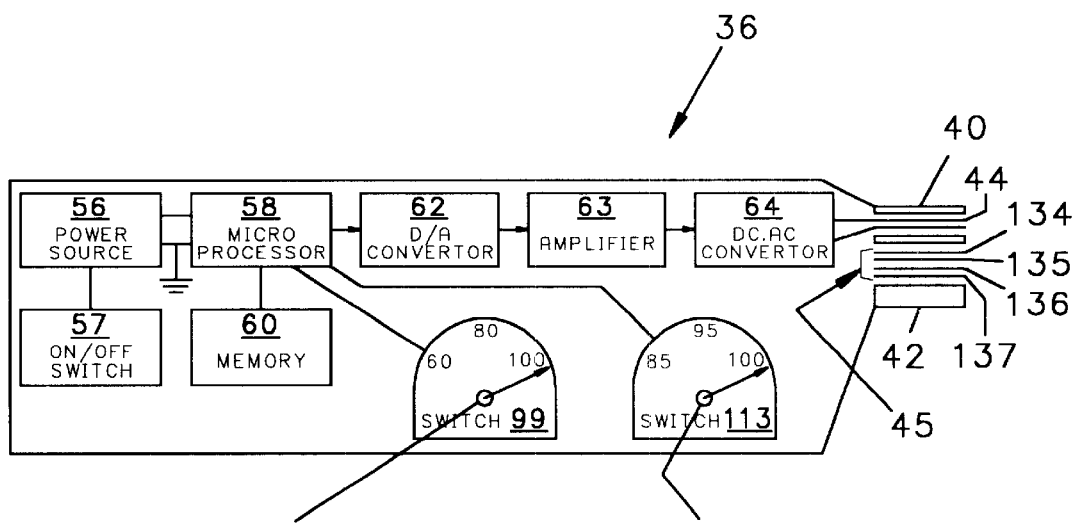
FIG. 4 is a block diagram of an arterial blood flow simulator in accordance with the present invention.

Referring further to FIG. 4, the blood flow simulator 36 of the present invention includes a power source 56, such as a nine volt battery for operating the various components of the device, an on/off switch 57, a microprocessor 58 including a programmed memory 60 for retaining a wave form that corresponds to a precise arterial blood flow amplitude and heart rate. The wave form is stored in a digitalized format and is directed by the microprocessor 58 to a digital to analog converter 62 which converts the digitalized wave form to a pulsating direct current. The pulsating direct current simulates human arterial blood flow rates through an artificial appendage 38. The direct current wave form is directed through an amplifier 63 and into a DC to AC converter 64 which converts the DC wave to an AC wave form needed to drive the light valve 44.

In the preferred embodiment, the simulator 36 includes a first selector knob 66 which can be moved through a plurality of settings each of which configures the microprocessor to modify the frequency of the wave form stored in the memory 60 to correspond to a different pulse rate of a patient. In the configuration depicted, the first selector knob 66 can be set to one of three simulated pulse rates shown as 60, 80 and 100 pulses per minute. The device 36 includes a second selector knob 68 in which the amplitude of the wave form emitted by the microprocessor 58 and, therefore, the amplitude of the wave form directed to the light valve 44 is adjusted to one of a plurality of settings, each of which correspond to given saturation percentages of hemoglobin of oxygenated blood. In the embodiment depicted, the second selector knob 68 can be set to one of three percentages of oxygenation, namely, 85 percent, 95 percent, and 100 percent.

Figure 5:
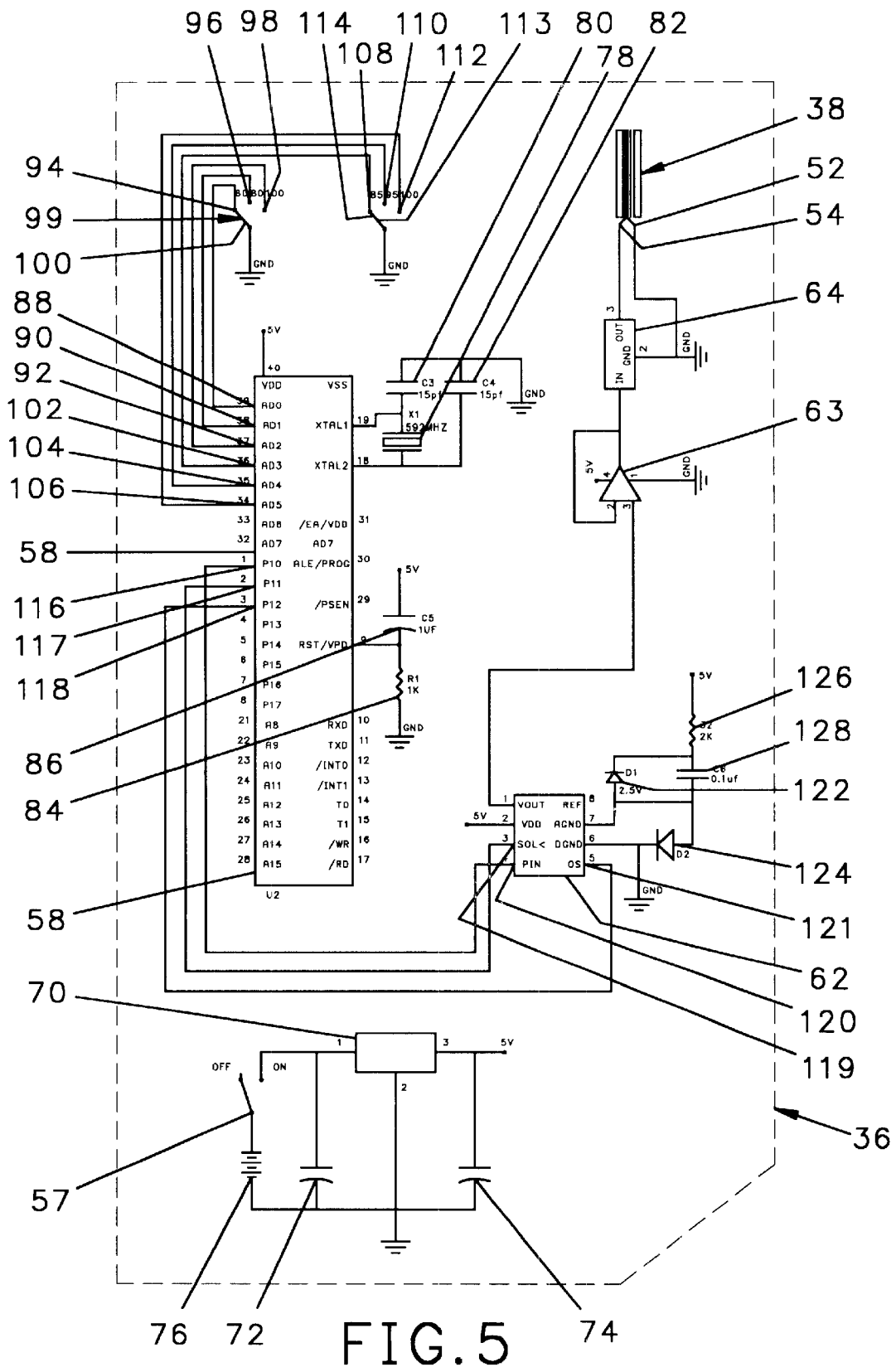
FIG. 5 is a schematic diagram of the signal generating circuit for the device shown in FIG. 4.

Referring to FIG. 5, the power source 56 includes a voltage regulator 70, such as provided by National Semiconductor as No. LM78MO5, is connected to capacitors 72, 74 as prescribed by the manufacturer for converting the output of a nine volt battery 76 to five volts which is required to operate the other elements of the device. The on/off switch 57 connects or disconnects the battery 76 into the circuit for the power source 56.

The heart of the device 36 is a microprocessor 58 which may be an Intel Part No. 87C51 and includes the memory 60. Attached to the microprocessor 58 are a crystal 78, capacitors 80, 82 and a resistor 84 all of which are prescribed by the manufacturer to provide an internal clock. A fifth capacitor 86 is also prescribed by the manufacturer to initialize the microcomputer when the unit is turned on. Three contacts 88, 90, 92 are connected to the contact points 94, 96, 98, respectively, of a first rotary switch 99 the shaft of which is attached to the first selector knob 66 and the rotatable contact 100 thereof is connected to ground. Similarly, three other contacts 102, 104, 106 of the microprocessor 58 are connected to the contacts 108, 110, 112 of a second rotary switch 113, the shaft of which is attached to the second selector knob 68, and the rotatable contact 114 of which is also connected to ground. The position of the selector switches 66, 68 is determined by the microprocessor by sensing when the contacts 88, 90, 92 and 102, 104, 106, respectively, are connected to ground.

The memory 60 is incorporated into the microprocessor 58, and the wave form is emitted by the microprocessor 58 through output connectors 116, 117, 118 which are connected to contacts 120, 119, 121, respectively, of the digital to analog converter 62. Where the digital to analog converter is a Sipex No. SP9600, the contacts 119, 120, 121 are labelled SCLK, DIN and CS, respectively. The digital to analog converter 62 has diodes 122, 124, resistor 126 and a capacitor 128 which are specified by the manufacturer for the proper operation of the IC. The converter 64 converts the digital wave form from the microprocessor to an analog wave form which simulates the human arterial blood flow rate, and also adds a DC bias voltage to the wave form.

The output from the digital to analog converter 62 is directed though an amplifier 63 such as made by Analog Devices. The output from the amplifier 63 is then directed through a DC to AC converter 64 such as made by Elstar of Japan. This component produces a two KHz carrier wave which can be varied between 60 and 120 volts rms depending on the DC voltage input into the amplifier 64 and modulated onto the carrier wave is the analog wave from the computer 58. The output of the DC to AC converter 64 is then applied across the contacts 52, 54 of the light valve 44. When an AC voltage signal is applied across the valve 44, the PDLC film thereof will become clear and allow most of the light that strikes the surface thereof to pass through. When the AC voltage is reduced, the PDLC will reflect or backscatter some of the light striking the PDLC film 46 and reduce the amount of light being received by the sensor 28 thereby simulating arterial blood flowing through the appendage.

As can be seen, the first rotary switch 99 which is connected with selector knob 66 alters the frequency rate of the wave emitted from the microprocessor 58 and thereby simulate a plurality of human heart rates, such as 60, 80 and 100 pulses per minute. Similarly, the second rotary switch 113 which is connected to the second selector knob 68 alters the amplitude of the wave emitted by the microprocessor 58 to thereby regulate the light conductivity range of the valve 44. The second rotary switch 113, therefore, regulates the light conductivity of the appendage 38 to simulate the conductivity of a human appendage which is receiving arterial blood flow having any of a plurality of selected percentages of oxygenation. In the embodiment depicted, the device may be used to simulate an 85 percent oxygenation of arterial blood flow, 95 percent, and 100 percent.

Within the simulated appendage 38, a 30 percent reabsorbing filter 45 constructed of four adjacent layers of cellophane 134, 135, 136, 137 is placed parallel to the PDLC film 46 to lower the overall percentage of red light that passes through the simulated appendage 38 and modifies the reflection path by backscattered red light without significantly affecting the infrared light. The interfaces between the layers 134, 135, 136, 137 of cellophane provide refraction surfaces which contribute to the scattering of red light. When the PDLC 46 is not energized, and has a minimum of transparency, approximately 30 percent of the red light and infrared light is backscattered into the red absorbing filter. The backscattering lengthens the path of the light and thereby reduces the light passing through the appendage. In contrast, when the PDLC 46 is energized it becomes nearly transparent and a minimum amount of red light is backscattered. Infrared light is not significantly affected by the filter 45, therefore, the PDLC changes the ratio of red light to infrared light.

To use the device 36, the artificial appendage 38 is inserted between the jaws 12, 14 of a pulse oximeter 10 and the switch 57 turned on. The selector knob 66 is adjusted such that the microprocessor 58 generates a wave form corresponding to a heart beat rate of 60, 80 or 100 which is then directed to the artificial appendage 38. The second selector knob 68 is adjusted such that the amplitude of the wave emitted from the microprocessor 58 changes the light permeability of the valve 44 such that the artificial appendage 38 has a pulsating permeability which corresponds to the pulsating permeability of a human appendage receiving arterial blood flow having the selected percent of oxygenation. In the embodiment depicted, the second selector knob 68 can be used to select oxygenation percentages of 85 percent, 95 percent and 100 percent. By comparing the pulse rate of the device 36 to the output reading of the pulse oximeter 10, the accuracy of the pulse oximeter 10 to determine the pulse rate of a patient can be tested. Similarly, by comparing the oxygenation percentage as selected by the second selector knob 68 of the simulator 36 with the output reading of the pulse oximeter 10 for the percentage of oxygenation of the arterial blood flow, the accuracy of the pulse oximeter to read the oxygenation percentages can be tested.

While one embodiment of the present invention has been shown and described, it will be apparent to those skilled in the art that many changes and modifications may be made without departing from the true spirit and scope of the present invention. It is the intent of the appended claims to cover all such changes and modifications which fall within the true spirit and scope of the invention.

What is claimed:

1. An arterial blood flow simulator comprising a body comprising material at least partially transparent to red and infrared lights, signal generating means for generating an electric signal having an amplitude corresponding to a given arterial blood flow oxygenation, and said body further comprising light valve means including polymer dispersed liquid crystal material responsive to said electronic signal for varying the amount of light passing through said body, whereby said body will simulate the light absorption of an appendage of the human body having an arterial blood flow passing therethrough where said arterial blood flow has a given percentage of oxygenation of the hemoglobin.

2. The arterial blood flow simulator of claim 1 wherein said body is shaped and sized to be at least partially received between a light source and a light sensor of a pulse oximeter.

3. The arterial blood flow simulator of claim 1 wherein said signal generating means further comprises, a microprocessor having a memory, a digitalized wave stored in said memory of said microprocessor, control means for modifying said amplitudes of said electric signal whereby said amplitude of said signal can be selected to cause said body to simulate any one of a plurality of percentages of oxygenation of the hemoglobin.

4. The arterial blood flow simulator of claim 1 wherein, said electric signal has a frequency corresponding to a given blood flow rate.

5. The arterial blood flow simulator of claim 3 wherein, said electric signal has a frequency corresponding to a given flow rate, and said signal generating means further comprises second control means for modifying said frequency of said electric signal whereby said frequency of said electric signal can be selected to simulate any one of a plurality of heart rates of a patient.

6. An arterial blood flow simulator comprising, a body comprising material at least partially transparent to red and infrared lights, signal generating means for generating an electric signal having a frequency corresponding to a given blood flow rate, and said body further comprising a light valve including polymer dispersed liquid crystal material responsive to said electronic signal for varying the amount of light passing through said body whereby said body will simulate the light absorption of an appendage of the human body having a given arterial blood flow rate passing therethrough.

7. The arterial blood flow simulator of claim 6 wherein said signal generating means further includes, a microprocessor having a memory, a digitalized wave stored in said memory of said microprocessor memory, control means for modifying said frequency of electric signal whereby said frequency of said electric signal can be selected to simulate any one of a plurality of heart rates of a patient.

* * * * *